(12) United States Patent
Lancaster

(10) Patent No.: US 7,262,277 B2
(45) Date of Patent: Aug. 28, 2007

(54) ANTAGONISTIC ANTI-HFAS LIGAND HUMAN ANTIBODIES AND FRAGMENTS THEREOF

(75) Inventor: Joanne Sloan Lancaster, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 311 days.

(21) Appl. No.: 10/506,743

(22) PCT Filed: Mar. 12, 2003

(86) PCT No.: PCT/US03/06155

§ 371 (c)(1), (2), (4) Date: Sep. 3, 2004

(87) PCT Pub. No.: WO03/079750

PCT Pub. Date: Oct. 2, 2003

(65) Prior Publication Data

US 2005/0106140 A1    May 19, 2005

Related U.S. Application Data

(60) Provisional application No. 60/367,054, filed on Mar. 21, 2002, provisional application No. 60/409,768, filed on Sep. 10, 2002.

(51) Int. Cl.
  *C12P 21/08* (2006.01)
(52) U.S. Cl. .............................. 530/387.3; 424/135.1; 424/141.1
(58) Field of Classification Search ..................... None
  See application file for complete search history.

(56) References Cited

U.S. PATENT DOCUMENTS 6,096,312 A  8/2000  Nakamura et al.
6,114,507 A  9/2000  Shirakawa et al.
6,348,334 B1  2/2002  Nagata et al.

FOREIGN PATENT DOCUMENTS

WO    WO95/18819    7/1995

OTHER PUBLICATIONS

Nisihara, T.; Ushio, Y.; Higuchi, H.; Kayagaki, N.; Yamaguchi, N.; Soejima, K.; Matsuo, S.; Maeda, H.; Eda, Y.; Okumura, K.; and Yagita, H. Humanization and epitope mapping of neutralizing anti-human Fas ligand monoclonal antibodies: structural insights into Fas/Fas ligand interaction. 2001. Journal of Immunology, vol. 167, pp. 3266-3275.*

Rudikoff, S., Giusti, A.M., Cook, W.D., and Scharff, M.D. Single amino acid substitution altering antigen-binding specificity. 1982 Proceedings of the National Academy of Sciences. vol. 79, pp. 1979-1983.*

Tanaka, et al., "Expression of the functional soluble form of human FAS ligand in activated lymphocytes" *The EMBO J.* vol. 14(6): 1129-1135 (1995).

Suda, et al., "Expression of the Fas Ligand in Cells of T Cell Lineage" *J. Immunology*, vol. 154: 3806-13 (1995).

Hanabuchi, et al, "Fas and its ligand in a general mechanism of T-cell mediated cytotoxity" *Proc., Natl. Acad. Sci. USA*, vol. 91:4930-4 (1994).

Kayagaki, et al., "Metalloproteinase-mediated Release of Human Fas Ligand", *J. Exp. Med.*, vol. 182:1777-83 (1995).

Elovaara, et al., "Upregulated expression of Fas ligand in brain through the spectrum of HIV-1 infection" *Acta Neuropathologica*, vol. 98(4): 355-62 (1999).

Nagata, et al., "The Fas Death Factor" *Science* vol. 267: 1449-56 (1995).

Arase, et al., "Fas-mediated Cytotoxicity by Freshly Isolated Natural Killer Cells" *J. Exp. Med.* vol. 181:1235-8 (1995).

Yagita, et al., "Fas-mediated Cytotoxicity—A New Immunoregulatory and Pathogenic Function of the Th1 CD4+ T Cells" *Immunol. Rev.* vol. 146:223-39 (1995).

Krammer, et al., "The Role of APO-1-Mediated Apoptosis in the Immune System" *Immunol. Rev.* vol. 142:175-91 (1994).

Mariani, et al., "Regulation of cell surface APO-1/Fas (CD95) ligand expression by metallopropteases" *Eur. J. Immunol.* vol. 25:2303-2307 (1995).

Nagata, "Fas Ligand-Induced Apoptosis" *Annu. Rev. Genet*, vol. 33: 29-55 (1999).

Leroy, X, et al., "Immunohistochemical detection of Fas and Fas ligand in sarcomatoid renal cell carcinoma" *APMIS*, vol. 109 :469-73 (2001).

Miwa, et al., "Therapeutic effect of an anti-Fas ligand mAb on lethal graft-versus-host disease" *International Immunology*, vol. 11(6): 925-931 (1999).

Nakayama, et al., "Fas/Fas Ligand Interactions Play an Essential Role in the Initiation of Murine Autoimmune Diabetes" *Diabetes*, vol. 51: 1391-97 (2002).

* cited by examiner

*Primary Examiner*—Larry R. Helms
*Assistant Examiner*—Anne M. Gussow
(74) *Attorney, Agent, or Firm*—Alejandro Martinez

(57) ABSTRACT

Human antibodies, preferably recombinant human antibodies that specifically bind to human Fas Ligand (hFasL) are disclosed. These antibodies have high affinity for hFasL, a slow off rate for hFasL dissociation and neutralize a Fas Ligand activity in vitro and in vivo. An antibody of the invention can be a full-length antibody or an antigen-binding portion thereof. The antibodies, or antigen-binding portions, of the invention are useful for neutralizing Fas Ligand activity, e.g., in a human subject suffering from a disorder in which hFas Ligand activity is detrimental. Nucleic acids, vectors and host cells for expressing the recombinant anti-hFasL human antibodies, and the methods for synthesizing the recombinant human antibodies are also encompassed by the invention.

11 Claims, No Drawings

SEQUENCE LISTING

<160> NUMBER OF SEQ ID NOS: 24

<210> SEQ ID NO 1
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 1

```
gaa att gtg ttg acg cag tct cca ggc acc ctg tct ttg tct cca ggg        48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc        96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc       144
Tyr Leu Ala Trp Tyr Gln Gln Lys Pro Gly Gln Ala Pro Arg Leu Leu
        35                  40                  45
```

```
atc tat ggt gca tcc agc agg gcc act ggc atc cca gac agg ttc agt       192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag       240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca ccg       288
Pro Glu Asp Phe Ala Val Tyr Tyr Cys Gln Gln Tyr Gly Ser Ser Pro
                 85                  90                  95 tgg acg ttc ggc caa ggg acc aag gtg gaa atc aaa cga act gtg gct       336
Trp Thr Phe Gly Gln Gly Thr Lys Val Glu Ile Lys Arg Thr Val Ala
            100                 105                 110 gca cca tct gtc ttc atc ttc ccg                                       360
Ala Pro Ser Val Phe Ile Phe Pro
        115                 120

<210> SEQ ID NO 2
<211> LENGTH: 120
<212> TYPE: PRT
<213> ORGANISM: Homo sapiens

<400> SEQUENCE: 2

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys Arg Thr Val Ala
            100                 105                 110

Ala Pro Ser Val Phe Ile Phe Pro
        115                 120

<210> SEQ ID NO 3
<211> LENGTH: 36
<212> TYPE: DNA
<213> ORGANISM: Homo sapiens
<220> FEATURE:
<221> NAME/KEY: CDS
<222> LOCATION: (1)..(36)

<400> SEQUENCE: 3 agg gcc agt cag agt gtt agc agc agc tac tta gcc                        36
Arg Ala Ser Gln Ser Val Ser Ser Ser Tyr Leu Ala
 1               5                  10

<210> SEQ ID NO 4
<211> LENGTH: 12
<212> TYPE: PRT
<213> ORGANISM: Homo sapiens

<400> SEQUENCE: 4

Arg Ala Ser Gln Ser Val Ser Ser Ser Tyr Leu Ala
 1               5                  10
```

<210> SEQ ID NO 5
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 5

```
ggt gca tcc agc agg gcc act                                              21
Gly Ala Ser Ser Arg Ala Thr
1               5
```

<210> SEQ ID NO 6
<211> LENGTH: 7
<212> TYPE: PRT
<213> ORGANISM: Homo sapiens

<400> SEQUENCE: 6

```
Gly Ala Ser Ser Arg Ala Thr
1               5
```

<210> SEQ ID NO 7
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 7

```
cag cag tat ggt agc tca ccg tgg acg                                      27
Gln Gln Tyr Gly Ser Ser Pro Trp Thr
1               5
```

<210> SEQ ID NO 8
<211> LENGTH: 9
<212> TYPE: PRT
<213> ORGANISM: Homo sapiens

<400> SEQUENCE: 8

```
Gln Gln Tyr Gly Ser Ser Pro Trp Thr
1               5
```

<210> SEQ ID NO 9
<211> LENGTH: 396
<212> TYPE: DNA
<213> ORGANISM: Homo sapiens
<220> FEATURE:
<221> NAME/KEY: CDS
<222> LOCATION: (1)..(396)

<400> SEQUENCE: 9

```
cag gtg cag ctg gtg cag tct gga gct gag gtg aag aag cct ggg gcc         48
Gln Val Gln Leu Val Gln Ser Gly Ala Glu Val Lys Lys Pro Gly Ala
1               5                   10                  15 tca gtg aag gtc tcc tgc aag gct tct ggt tac atc ttt atc aga cat         96
Ser Val Lys Val Ser Cys Lys Ala Ser Gly Tyr Ile Phe Ile Arg His
            20                  25                  30 ggt atc acc tgg gtg cga cag gcc cct gga caa ggg ctt gag tgg atg        144
Gly Ile Thr Trp Val Arg Gln Ala Pro Gly Gln Gly Leu Glu Trp Met
        35                  40                  45 gga tgg atc aac gct tac aat ggt aac aca aac tat gca cag aag gtc        192
Gly Trp Ile Asn Ala Tyr Asn Gly Asn Thr Asn Tyr Ala Gln Lys Val
    50                  55                  60
```

-continued

```
cag ggc aga gtc acc atg acc aca gac aaa tcc acg agc aca gcc tac      240
Gln Gly Arg Val Thr Met Thr Thr Asp Lys Ser Thr Ser Thr Ala Tyr
 65                  70                  75                  80 atg gag ctg agg agc ctg aga tct gac gac gcg gcc gtg tat tat tgt      288
Met Glu Leu Arg Ser Leu Arg Ser Asp Asp Ala Ala Val Tyr Tyr Cys
                 85                  90                  95 gcg aga gag act atg gtt cgg gga gtt ccc ctt gac tac tgg ggc cag      336
Ala Arg Glu Thr Met Val Arg Gly Val Pro Leu Asp Tyr Trp Gly Gln
            100                 105                 110 gga acc ctg gtc acc gtc tcc tca gct tcc acc aag ggc cca tca gtc      384
Gly Thr Leu Val Thr Val Ser Ser Ala Ser Thr Lys Gly Pro Ser Val
        115                 120                 125 ttc ccc ctg gcg                                                      396
Phe Pro Leu Ala
    130
```

<210> SEQ ID NO 10
<211> LENGTH: 132
<212> TYPE: PRT
<213> ORGANISM: Homo sapiens

<400> SEQUENCE: 10

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ile Phe Ile Arg His
             20                  25                  30

Gly Ile Thr Trp Val Arg Gln Ala Pro Gly Gln Gly Leu Glu Trp Met
         35                  40                  45

Gly Trp Ile Asn Ala Tyr Asn Gly Asn Thr Asn Tyr Ala Gln Lys Val
     50                  55                  60

Gln Gly Arg Val Thr Met Thr Thr Asp Lys Ser Thr Ser Thr Ala Tyr
 65                  70                  75                  80

Met Glu Leu Arg Ser Leu Arg Ser Asp Asp Ala Ala Val Tyr Tyr Cys
                 85                  90                  95

Ala Arg Glu Thr Met Val Arg Gly Val Pro Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala
    130
```

<210> SEQ ID NO 11
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 11

```
aga cat ggt atc acc                                                   15
Arg His Gly Ile Thr
 1               5
```

<210> SEQ ID NO 12
<211> LENGTH: 5
<212> TYPE: PRT
<213> ORGANISM: Homo sapiens

<400> SEQUENCE: 12

Arg His Gly Ile Thr

<210> SEQ ID NO 13
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 13

```
tgg atc aac gct tac aat ggt aac aca aac tat gca cag aag gtc cag      48
Trp Ile Asn Ala Tyr Asn Gly Asn Thr Asn Tyr Ala Gln Lys Val Gln
1               5                   10                  15 ggc                                                                  51
Gly
```

<210> SEQ ID NO 14
<211> LENGTH: 17
<212> TYPE: PRT
<213> ORGANISM: Homo sapiens

<400> SEQUENCE: 14

```
Trp Ile Asn Ala Tyr Asn Gly Asn Thr Asn Tyr Ala Gln Lys Val Gln
1               5                   10                  15

Gly
```

<210> SEQ ID NO 15
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 15

```
gag act atg gtt cgg gga gtt ccc ctt gac tac                          33
Glu Thr Met Val Arg Gly Val Pro Leu Asp Tyr
1               5                   10
```

<210> SEQ ID NO 16
<211> LENGTH: 11
<212> TYPE: PRT
<213> ORGANISM: Homo sapiens

<400> SEQUENCE: 16

```
Glu Thr Met Val Arg Gly Val Pro Leu Asp Tyr
1               5                   10
```

<210> SEQ ID NO 17
<211> LENGTH: 396
<212> TYPE: DNA
<213> ORGANISM: Homo sapiens
<220> FEATURE:
<221> NAME/KEY: CDS
<222> LOCATION: (1)..(396)

<400> SEQUENCE: 17

```
cag gtg cag ctg gtg cag tct gga gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct ggt tac atc ttt atc agt cat      96
Ser Val Lys Val Ser Cys Lys Ala Ser Gly Tyr Ile Phe Ile Ser His
            20                  25                  30 ggt atc agt tgg gtg cga cag gcc cct gga caa ggg ctt gag tgg atg     144
```

```
Gly Ile Ser Trp Val Arg Gln Ala Pro Gly Gln Gly Leu Glu Trp Met
         35                  40                  45 gga tgg atc aac gct tac agt ggt aac aca aac tat gca cag aag ctc    192
Gly Trp Ile Asn Ala Tyr Ser Gly Asn Thr Asn Tyr Ala Gln Lys Leu
 50                  55                  60 cag ggc aga gtc acc atg acc aca gac aga tcc acg agc aca gcc tac    240
Gln Gly Arg Val Thr Met Thr Thr Asp Arg Ser Thr Ser Thr Ala Tyr
 65                  70                  75                  80 atg gag ctg agg agc ctg aga tct gac gac acg gcc gtg tat tac tgt    288
Met Glu Leu Arg Ser Leu Arg Ser Asp Asp Thr Ala Val Tyr Tyr Cys
                 85                  90                  95 gcg aga gag act atg gtt cgg gga gtt ccc tgt gac tac tgg ggc cag    336
Ala Arg Glu Thr Met Val Arg Gly Val Pro Cys Asp Tyr Trp Gly Gln
             100                 105                 110 gga acc ctg gtc acc gtc tcc tca gct tcc acc aag ggc cca tcc gtc    384
Gly Thr Leu Val Thr Val Ser Ser Ala Ser Thr Lys Gly Pro Ser Val
         115                 120                 125 ttc ccc ctg gcg                                                    396
Phe Pro Leu Ala
    130

<210> SEQ ID NO 18
<211> LENGTH: 132
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Ile Ser His
                 20                  25                  30

Gly Ile Ser Trp Val Arg Gln Ala Pro Gly Gln Gly Leu Glu Trp Met
             35                  40                  45

Gly Trp Ile Asn Ala Tyr Ser Gly Asn Thr Asn Tyr Ala Gln Lys Leu
 50                  55                  60

Gln Gly Arg Val Thr Met Thr Thr Asp Arg Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Thr Met Val Arg Gly Val Pro Cys Asp Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala
    130

<210> SEQ ID NO 19
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 19 agt cat ggt atc agt                                                 15
Ser His Gly Ile Ser
 1               5

<210> SEQ ID NO 20
```

```
<211> LENGTH: 5
<212> TYPE: PRT
<213> ORGANISM: Homo sapiens

<400> SEQUENCE: 20

Ser His Gly Ile Ser
1               5

<210> SEQ ID NO 21
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 21 tgg atc aac gct tac agt ggt aac aca aac tat gca cag aag ctc cag     48
Trp Ile Asn Ala Tyr Ser Gly Asn Thr Asn Tyr Ala Gln Lys Leu Gln
1               5                   10                  15 ggc                                                                 51
Gly

<210> SEQ ID NO 22
<211> LENGTH: 17
<212> TYPE: PRT
<213> ORGANISM: Homo sapiens

<400> SEQUENCE: 22

Trp Ile Asn Ala Tyr Ser Gly Asn Thr Asn Tyr Ala Gln Lys Leu Gln
1               5                   10                  15

Gly

<210> SEQ ID NO 23
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 23 gag act atg gtt cgg gga gtt ccc tgt gac tac                         33
Glu Thr Met Val Arg Gly Val Pro Cys Asp Tyr
1               5                   10

<210> SEQ ID NO 24
<211> LENGTH: 11
<212> TYPE: PRT
<213> ORGANISM: Homo sapiens

<400> SEQUENCE: 24

Glu Thr Met Val Arg Gly Val Pro Cys Asp Tyr
1               5                   10
```

ANTAGONISTIC ANTI-HFAS LIGAND HUMAN ANTIBODIES AND FRAGMENTS THEREOF

This application is the National Stage application of International Application No. PCT/US03/06155, filed Mar. 12, 2003, which claims the benefit of US provisional application 60/367,054 filed Mar. 21, 2002 and US provisional application 60/409,768, filed Sep. 10, 2002.

Fas ligand ("FasL") is a protein with an activity to induce apoptosis of a Fas antigen ("Fas")-expressing cell. Apoptosis of the Fas antigen-expressing cells is believed to be induced by binding of FasL with Fas on the cell surface, which results in the transfer of an apoptosis signal to the cell via the Fas antigen. The nucleic acid and protein sequences of FasL of human, mouse and rat origin are disclosed in U.S. Pat. No. 6,348,334 (incorporated herein by reference).

Human Fas Ligand ("hFasL") is a 40-kDa amino acid, type II membrane-bound protein that is a member of the TNF family. Membrane-bound FasL can be cleaved by metalloproteinases to generate soluble FasL, which is primarily a non-covalently linked homotrimer (Mariani, et al., *Eur. J. Immunol.* 25:2303-7 (1995); Kayagaki, et al., *J. Exp. Med.* 182:1777-83 (1995); Tanaka, et al., *EMBO* 14(6): 1129-35 (1995));. Soluble FasL appears to be less cytotoxic than membrane-associated FasL (Nagata, *Annu. Rev. Genet.* 33:29-55 (1999)).

FasL is predominantly expressed on activated T cells and natural killer (NK) cells, while Fas is expressed on various types of cells (Hanabuchi, et al., *Proc. Natl. Acad. Sci. USA* 91:4930-4 (1994); Suda, et. al., *J. Immunol.* 154:3806-13 (1995); Arase, et. al., *J. Exp. Med.* 181:1235-8 (1995)). The Fas-FasL signaling pathway is important in modulating immune responses by inducing cellular apoptosis. Recently, FasL was reported to be a potent chemoattractant for neutrophils, suggesting a pro-inflammatory function of this molecule. The Fas-FasL signaling pathway has also been implicated in the pathogenesis of multiple diseases, including autoimmune diseases, renal disorders, sepsis, viral hepatitis, HIV, influenza and graft-versus-host disease (see, e.g., Krammer, et al., *Immunol. Rev.* 142:175-91 (1994); Nagata and Golstein, *Science* 267:1449-56 (1995);Yagita, et al., *Immunol. Rev.* 146:223-39 (1995); Elovaara, et al., *Acta Neuropathologica,* 98(4):355-62 (1999); Leroy, X. et al., *APMIS,* 109(6):469-73, 2001).

Antibodies to hFasL comprising mouse antibody sequences, as well as chimeric antibody species having a fraction of a human antibody sequence, have been described (see, e.g., International Patent Publication No. WO 95/18819 and U.S. Pat. Nos. 6,114,507 and 6,348,334 and 6,096,312, incorporated herein by reference). However, immunogenicity problems remain with the use of chimeric antibodies. Producing humanized antibodies (i.e., chimeric) through recombinant DNA technology provides uncertain results, including antibodies with unpredictable binding affinities. U.S. Pat. No. 6,348,334 non-descriptively discloses antibodies directed at FasL, however, it does not specifically describe structural characteristics of such antibodies.

Human antibodies, as defined herein, are advantageous over non-human antibodies and humanized, chimeric antibodies for use in human therapy for several reasons. A human monoclonal antibody, i.e., an antibody that is fully human, is less likely to induce an immunological response in humans than antibodies that contain non-human portions. Furthermore, a human antibody is less likely to be recognized as a "foreign" antibody in humans. This will result in slower elimination of the human antibody from the body than a non-human or partially human antibody. Accordingly, a human antibody can be administered at lower doses or less often than non-human or partially human antibodies.

To minimize the potential for cross-species reactivity, the need exists for human antibodies against FasL, particularly human FasL, with high affinity binding to FasL and the capacity to disrupt or antagonize the activity of the Fas-FasL signaling pathway in vitro and in vivo. The present application discloses therapeutically useful human antibodies, and antigen-binding portions thereof, directed against hFasL and characterized by high affinity binding to hFasL polypeptides, slow dissociation kinetics, and the capacity to disrupt or antagonize at least one in vitro and/or in vivo activity associated with hFasL polypeptides.

The present invention provides isolated anti-hFasL human antibodies and antigen-binding portions thereof. The antibodies of the invention are characterized by high affinity binding to a hFasL polypeptide, slow dissociation kinetics, and the capacity to antagonize at least one in vitro and/or in vivo and/or in situ activity associated with a hFasL polypeptide.

The invention provides an isolated anti-hFasL human antibody, or antigen-binding portion thereof, comprising at least one polypeptide, preferably at least two polypeptides, with a sequence selected from the group consisting of the sequences shown in SEQ ID NO: 2, 4, 6, 8, 10, 12, 14, 16, 18, 20, 22, and 24. In a preferred embodiment, the invention provides an isolated anti-FasL human antibody, or antigen-binding portion thereof, comprising a light chain variable region (LCVR) comprising a polypeptide with the sequence shown in SEQ ID NO: 2. In a more preferred embodiment, the invention provides an isolated anti-hFasL human antibody, or antigen-binding portion thereof, comprising a LCVR comprising a polypeptide with the sequence shown in SEQ ID NO: 2 and further comprising a heavy chain variable region (HCVR) comprising a polypeptide with the sequence shown in SEQ ID NO: 10. In another preferred embodiment, the invention provides an isolated anti-hFasL human antibody, or antigen-binding portion thereof, having a LCVR comprising a polypeptide with the sequence shown in SEQ ID NO: 2 and further comprising a heavy chain variable region (HCVR) comprising a polypeptide with the sequence shown in SEQ ID NO: 18. In another preferred embodiment, the invention provides an isolated anti-hFasL human antibody, or antigen-binding portion thereof, comprising at least one polypeptide, preferably at least 2, 3, 4, 5 or 6 polypeptides, with a sequence selected from the group consisting of the sequences shown in SEQ ID NOs: 4, 6, 8, 12, 14, 16, 20, 22, and 24, wherein said polypeptide preferably exists in said antibody at the same CDR position as shown in Tables 1, 2 or 3 herein.

In another embodiment, the invention provides an isolated nucleic acid molecule comprising a polynucleotide encoding an anti-hFasL human antibody, or antigen-binding portion thereof, comprising at least one polypeptide, preferably at least two polypeptides, with a sequence selected from the group consisting of the sequences shown in SEQ ID NOs: 2, 4, 6, 8, 10, 12, 14, 16, 18, 20, 22, and 24. In a preferred embodiment, the invention provides an isolated nucleic acid molecule comprising a polynucleotide encoding an anti-hFasL human antibody, or antigen-binding portion thereof, comprising SEQ ID NO: 2. In a more preferred embodiment, the invention provides an isolated nucleic acid molecule comprising a polynucleotide encoding an anti-hFasL human antibody, or antigen-binding portion thereof, comprising the sequences shown in SEQ ID NOs: 2 and 10 or SEQ ID NOs:

2 and 18. In another preferred embodiment, the invention provides an isolated nucleic acid molecule comprising a polynucleotide encoding an anti-hFasL human antibody, or antigen-binding portion thereof, comprising at least one polypeptide, preferably at least 2, 3, 4, 5 or 6 polypeptides, with a sequence selected from the group consisting of the sequences shown in SEQ ID NOs: 4, 6, 8, 12, 14, 16, 20, 22, and 24, wherein said polypeptide preferably exists in said antibody at the same CDR position as shown in Tables 1, 2 or 3 herein.

In another embodiment, the invention provides an isolated nucleic acid molecule comprising a polynucleotide encoding an anti-hFasL human antibody, or antigen-binding portion thereof, comprising at least one polynucleotide, preferably at least two polynucleotides, with a sequence selected from the group consisting of the sequences shown in SEQ ID NOs: 1, 3, 5, 7, 9, 11, 13, 15, 17, 19, 21, and 23. In a preferred embodiment, the invention provides an isolated nucleic acid molecule comprising a polynucleotide encoding an anti-hFasL human antibody, or antigen-binding portion thereof, comprising a polynucleotide with a sequence as shown in SEQ ID NO: 1. In a more preferred embodiment, the invention provides an isolated nucleic acid molecule comprising a polynucleotide encoding an anti-hFasL human antibody, or antigen-binding portion thereof, comprising polynucleotides with the sequences shown in SEQ ID NOs: 2 and 10 or SEQ ID NOs: 2 and 18. In another preferred embodiment, the invention provides an isolated nucleic acid molecule comprising a polynucleotide encoding an anti-hFasL human antibody, or antigen-binding portion thereof, comprising at least one polynucleotide, preferably at least 2, 3, 4, 5 or 5 polynucleotides, with a sequence selected from the group consisting of SEQ ID NO: 3, 5, 7, 11, 13, 15, 19, 21, and 23, wherein said polynucleotide encodes a polypeptide that preferably exists in said antibody at the same CDR position as shown in Tables 1, 2 or 3 herein.

In another embodiment, the invention provides a vector, preferably a recombinant expression vector, comprising a polynucleotide of the invention.

In another embodiment, the present invention provides a host cell into which a vector, preferably a recombinant expression vector, of the invention has been introduced.

In another embodiment, the present invention provides host cell into which a vector, preferably a recombinant expression vector, of the invention has been incorporated in whole or in part into the host cell chromosome.

In another embodiment, the present invention provides a method of synthesizing an anti-hFasL human antibody, or antigen-binding portion thereof, comprising culturing a host cell of the invention in culture media such that an anti-hFasL human antibody, or antigen-binding portion thereof, of the present invention is expressed in the cell.

In another embodiment, the present invention provides a process for preparing a polypeptide of the invention, i.e., an anti-hFasL human antibody, or antigen-binding portion thereof, comprising culturing a suitable host cell of the invention comprising an expression vector of the invention under conditions promoting expression of the polypeptide and purifying said polypeptide. It is contemplated that such purification may be from the host cell, the culture media in which the host cell is grown, or both.

In another embodiment, the present invention provides a method for inhibiting hFasL activity comprising contacting hFasL with an anti-hFasL human antibody, (or antigen-binding portion thereof) of the invention.

In another embodiment, the invention provides a pharmaceutical composition comprising an anti-hFasL human antibody, or antigen-binding portion thereof, of the invention. It is contemplated that a pharmaceutical composition of the invention may comprise greater than one anti-hFasL human antibodies of the invention.

A pharmaceutical composition of the invention may further comprise a pharmaceutically acceptable carrier.

The invention also embodies a method for neutralizing a FasL activity and a method of treating or preventing a disorder in which a FasL activity is detrimental, comprising delivering to a subject, in need thereof, a therapeutically effective amount of a pharmaceutical composition of the invention. In preferred embodiments, the disorder in which FasL activity is detrimental is systemic inflammatory response syndrome, sepsis, multiple organ dysfunction syndrome, acute respiratory distress syndrome, severe sepsis, trauma, graft-versus-host disease, organ rejection associated with organ transplant, multiple sclerosis, idiopathic pulmonary fibrosis, osteoarthritis, inflammatory bowel disease, Crohn's disease, ulcerative colitis, acute myocardial infarction, cardiomyopathy, cardiac reperfusion injury, diabetes, cancers (preferably cancer types which express or overexpress FasL as a mechanism of evading the immune response; contemplated cancer types include but are not limited to, breast cancer, melanoma, ovarian cancer, colon cancer, NSCLC, lymphoma and hepatocellular carcinoma), human immunodeficiency virus, influenza virus, hepatic disorders including but not limited to, fulminant viral hepatitis B or C, chronic hepatitis C virus, chronic hepatitis B virus, alcoholic hepatitis, hepatic cirrhosis, or renal disorders including, but not limited to, chronic renal disease, acute renal disease and diabetic nephropathy.

In yet another embodiment, the invention provides a human antibody, and compositions comprising the human antibody, produced by the hybridoma deposited as ATCC PTA-4017 or the hybridoma deposited on 29 Jan. 2002 as ATCC PTA-4018 with the American Type Culture Collection, Manassas, Va.

The invention is not limited to the particular embodiments described below, as variations of the particular embodiments may be made and still fall within the scope of the appended claims. Instead, the scope of the present invention will be established by the appended claims.

An antibody is an immunoglobulin molecule comprised of four polypeptide chains, two heavy (H) chains (about 50-70 kDa when full length) and two light (L) chains (about 25 kDa when full length) inter-connected by disulfide bonds. Light chains are classified as kappa and lambda. Heavy chains are classified as gamma, mu, alpha, delta, or epsilon, and define the antibody's isotype as IgG, IgM, IgA, IgD, and IgE, respectively. Each heavy chain is comprised of a heavy chain variable region (abbreviated herein as HCVR) and a heavy chain constant region. The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions (Kabat, "Sequences of Proteins of Immunological Interest," National Institutes of Health, Bethesda, Md. (1987 and 1991); Chothia, et al., *J. Mol. Biol.* 196:901-17 (1987); Chothia, et al., *Nature* 342:878-83 (1989)). The functional ability of the antibody to bind a particular antigen is largely determined by the CDRs.

The term "antibody," as used herein, refers to a monoclonal antibody per se. A monoclonal antibody can be a human antibody, chimeric antibody and/or humanized antibody. A monoclonal antibody can be a Fab fragment, Fab' fragment or F(ab')2 fragment of a human antibody, chimeric antibody and/or humanized antibody. Furthermore, a monoclonal antibody can be a single chain FV fragment.

The term "human antibody," as used herein, is (i) an intact antibody, (ii) a substantially intact antibody, (iii) a portion of an antibody comprising an antigen-binding site, or (iv) a portion of an antibody comprising a Fab fragment, Fab' fragment or F(ab')2, having variable and constant regions encoded by nucleic acid sequence information that occurs in the human germline immunoglobulin region or in recombined and/or mutated forms thereof whether or not said antibodies are produced in human cells. The term "human antibody" also includes a human antibody engineered to take the form of a single chain FV fragment.

Chimeric, humanized, or CDR-grafted antibodies, which contain at least one non-human Fc, FR, or CDR region, are not human antibodies as referred to herein.

The term "hFasL" refers to human Fas Ligand, a member of the tumor necrosis factor family of ligands described in Suda, et al., *Cell* 75:1169-78 (1993). The function of hFasL is described further in Krammer, et al, *Immunol. Rev.* 142: 175-91 (1994); Nagata and Golstein, *Science* 267(5203): 1449-56 (1995); and Yagita, et al., *Immunol. Rev.* 146:223-39 (1995). The term "Fas Ligand" is intended to encompass hFasL as well as homologs of hFasL derived from other species. The terms "hFasL" and "FasL" are intended to include forms thereof that can be prepared by standard recombinant expression methods or purchased commercially (Alexis® Biochemicals, Catalog #522-001) as well as generated synthetically.

The term "soluble," when used in conjunction with FasL, refers to a cleaved form of the "membrane-associated" or "membrane bound" form of FasL. Soluble FasL describes soluble fragments containing at least a portion of the extracellular domain of membrane bound FasL. Soluble FasL is generated by metalloproteinase cleavage at a specific site in the extracellular region of FasL, resulting in a soluble molecule (Hohlbaum, et al., *J. Exp. Med.* 191(7):1209-20 (2000); Tanaka, et al., *Nat. Med.* 2(3):317-22 (1996); and Kayagaki, et al, *J. Exp. Med.* 182(6):1777-83 (1995)). Like the membrane bound form, soluble FasL is capable of inducing apoptosis upon binding Fas.

The phrases "biological property" or "biological characteristic," or the terms "activity" or "bioactivity," in reference to an antibody or antibody fragment of the present invention, are used interchangeably herein and include, but are not limited to, epitope affinity and specificity (e.g., anti-hFasL human antibody binding to hFasL), ability to antagonize the activity of the targeted polypeptide in vivo and/or in vitro (e.g., FasL bioactivity), the in vivo stability of the antibody, and the immunogenic properties of the antibody. Other identifiable biological properties or characteristics of an antibody recognized in the art include, for example, cross-reactivity, (i.e., with non-human homologs of the targeted polypeptide, or with other proteins or tissues, generally), and ability to preserve high expression levels of protein in mammalian cells. The aforementioned properties or characteristics can be observed or measured using art-recognized techniques including, but not limited to ELISA, competitive ELISA, BIAcore® surface plasmon resonance analysis, in vitro and in vivo neutralization assays (e.g., Examples 1, 2, and 3), and immunohistochemistry with tissue sections from different sources including human, primate, or any other source as the need may be.

The term "epitope" as used herein refers to a region of a protein molecule to which an antibody can bind. An "immunogenic epitope" is defined as the part of a protein that elicits an antibody response when the whole protein is the immunogen. See, for instance, Geysen, et al., *Proc. Natl. Acad. Sci. USA* 81:3998-4002 (1984). An "antigen binding portion" of an antibody, as used herein, refers to a region of an antibody that interacts with or binds to an epitope to which the antibody binds when the antigen binding portion is comprised within an antibody. The antigen binding portion may exist outside the context of the full length antibody and still be considered to be an antigen binding portion of the antibody whether or not it still interacts with or binds to an epitope.

The term "inhibit" or "inhibiting" means neutralizing, antagonizing, prohibiting, preventing, restraining, slowing, disrupting, stopping, or reversing progression or severity of that which is being inhibited, e.g., including, but not limited to an activity, a disease or condition.

The term "isolated" when used in relation to a nucleic acid or protein (e.g., an antibody), refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature. Preferably, an "isolated antibody" is an antibody that is substantially free of other antibodies having different antigenic specificities (e.g., an isolated antibody that specifically binds hFas Ligand substantially free of antibodies that specifically bind antigens other than hFas Ligand polypeptide).

As used herein, the term "purified" or "to purify" means the result of any process which removes some contaminant from the component of interest, such as a protein or nucleic acid. The percent of a purified component is thereby increased in the sample. In preferred embodiments, the antibody will be purified (1) to greater than 95% by weight of antibody as determined by the Lowry method, and most preferably more than 99% by weight, and (2) to homogeneity by SDS-PAGE under reducing or non-reducing conditions using Coomassie blue, or preferably, silver stain.

The terms "Kabat numbering" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody (Kabat, et al., *Ann. NY Acad. Sci.* 190:382-93 (1971); Kabat, et al., *Sequences of Proteins of Immunological Interest*, Fifth Edition, U.S. Department of Health and Human Services, NIH Publication No. 91-3242 (1991)).

A polynucleotide is "operably linked" when it is placed into a functional relationship with another polynucleotide. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence.

Transgenic animals (e.g., mice) that are capable, upon immunization, of producing human antibodies in the absence of endogenous immunoglobulin production can be employed in the invention. Transfer of the human germline immunoglobulin gene array in such germline mutant mice will result in the production of human antibodies upon antigen challenge. See, e.g., Jakobovits, et al., *Proc. Natl. Acad. Sci. USA* 90:2551-5 (1993); Jakobovits, et al., *Nature* 362:255-8 (1993); Bruggemann, et al., *Year in Immun.* 7:33 (1993); *Nature* 148:1547-53 (1994), *Nature Biotechnology* 14:826 (1996); Gross, et al., *Nature* 404:995-9 (2000); and U.S. Pat. Nos. 5,877,397; 5,874,299; 5,814,318; 5,789,650; 5,770,429; 5,661,016; 5,633,425; 5,625,126; 5,569,825; and 5,545,806.

Human antibodies can also be produced in phage display libraries (Hoogenboom and Winter, *J. Mol. Biol.* 227:381-8 (1992)). The techniques of Cole, et al., and Boemer, et al., are also among those techniques available for the preparation of human monoclonal antibodies (Cole, et al., *Monoclonal Antibodies and Cancer Therapy*, Alan R. Liss, p. 77 (1985); and Boemer, et al., *J. Immunol.* 147:86-95 (1991)).

Recombinant human antibodies may also be subjected to in vitro mutagenesis (or, when an animal transgenic for human Ig sequences is used, in vivo somatic mutagenesis) and, thus, the amino acid sequences of the HCVR and LCVR regions of the recombinant antibodies are sequences that, while derived from those related to human germline HCVR and LCVR sequences, may not naturally exist within the human antibody germline repertoire in vivo.

The term "neutralizing" or "antagonizing" in reference to an anti-FasL antibody or the phrase "antibody that antagonizes (neutralizes) FasL activity" or "antagonizes (neutralizes) FasL" is intended to refer to an antibody, or antigen-binding portion thereof, whose binding to or contact with FasL results in inhibition of a biological activity induced by FasL polypeptides. Inhibition of FasL biological activity can be assessed by measuring one or more in vitro or in vivo indicators of FasL biological activity including, but not limited to, induction of FasL-mediated intracellular signaling, apoptosis, neutrophil chemotaxis, or inhibition of receptor binding in a FasL receptor binding assay. Indicators of FasL biological activity can be assessed by one or more of the several in vitro or in vivo assays known in the art. Preferably, the ability of an antibody to neutralize or antagonize FasL activity is assessed by inhibition of Fas-FasL mediated apoptosis.

The terms "individual," "subject," and "patient," used interchangeably herein, refer to a mammal, including, but not limited to, murine, simian, human, mammalian farm animals, mammalian sport animals, and mammalian pets.

The term "$K_{off}$" as used herein, refers to the off rate constant for dissociation of an antibody from the antibody/antigen complex. The dissociation rate constant ($K_{off}$) of an anti-hFasL human antibody can be determined by BIAcore® surface plasmon resonance as generally described in Example 3. Generally, BIAcore® analysis measures real-time binding interactions between ligand (recombinant FasL polypeptide immobilized on a biosensor matrix) and analyte (antibodies in solution) by surface plasmon resonance (SPR) using the BIAcore system (Pharmacia Biosensor, Piscataway, N.J.). SPR can also be performed by immobilizing the analyte (antibodies on a biosensor matrix) and presenting the ligand in solution. A low off rate for an antigen/antibody complex refers to a $K_{off}$ of $10^{-3}$ sec$^{-1}$ or less, preferably $10^{-4}$ sec$^{-1}$ or less, or even more preferably $10^{-5}$ sec$^{-1}$ or less.

The term "$K_D$," as used herein, refers to the equilibrium dissociation constant of a particular antibody-antigen interaction. For purposes of the present invention, $K_D$ may be determined as shown in Example 3. Antibodies with high avidity and/or high affinity binding with a particular epitope have a $K_D$ of $10^{-7}$ M or less, preferably $10^{-8}$ M or less, more preferably $10^{-9}$ M or less.

The term "vector" includes a nucleic acid molecule capable of transporting another nucleic acid to which it has been linked including, but not limited to, plasmids and viral vectors. Certain vectors are capable of autonomous replication in a host cell into which they are introduced while other vectors can be integrated into the genome of a host cell upon introduction into the host cell, and thereby, are replicated along with the host genome. Moreover, certain vectors are capable of directing the expression of genes to which they are operably linked. Such vectors are referred to herein as "recombinant expression vectors" (or simply "expression vectors").

The term "host cell" includes an individual cell or cell culture that can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the invention. A host cell which comprises a recombinant vector of the invention may also be referred to as a "recombinant host cell". Preferably the host cell is bacterial or mammalian; if mammalian, it is preferably a CHO, COS, NSO or 293 cell.

The present invention relates to human monoclonal antibodies that are specific for and neutralize a hFasL polypeptide, antigenic fragment thereof, or an hFasL activity. Also disclosed are antibody heavy and/or light chain fragments that are highly specific for, and neutralize a FasL polypeptide, antigenic fragment or epitope-bearing thereof, or an hFasL activity, preferably the binding of hFasL to Fas. This high specificity for binding FasL enables the anti-hFasL human antibodies, antigen-binding portions thereof, and human monoclonal antibodies with like specificity, to be immunotherapeutic to Fas-FasL associated diseases.

In one embodiment, the invention provides an isolated anti-hFasL human antibody, or antigen-binding portion thereof, comprising at least one, preferably at least two, of the amino acid sequences selected from the group consisting of SEQ ID NOs : 2, 4, 6, 8, 10, 12, 14, 16, 18, 20, 22, and 24. The sequences represented in SEQ ID NOs 4, 6, 8, 12, 14, 16, 20, 22 and 24, when present in an antibody of the invention are preferably positioned in the antibody of the invention at the same CDR location as depicted in Tables 1, 2 and 3 herein and as they are positioned in SEQ ID NO: 2 (for SEQ ID NOs: 4, 6 and 8), SEQ ID NO: 10 (for SEQ ID NOs: 12, 14, and 16) and SEQ ID NO: 18 (for SEQ ID NOs: 20, 22 and 24).

In a preferred embodiment, the invention provides an isolated anti-FasL human antibody, or antigen-binding portion thereof, that binds a soluble FasL polypeptide (or antigenic fragment thereof) with an equilibrium dissociation constant, $K_D$, of $2 \times 10^{-7}$ M or less, more preferably $2 \times 10^{-8}$ M or less and even more preferably $2 \times 10^{-9}$ M or less (as determined by solid phase BIAcore® surface plasmon resonance at room temperature), dissociates from a FasL polypeptide with a low $k_{off}$ rate constant, and has the capacity to antagonize a FasL polypeptide activity.

Another embodiment of the invention provides an isolated anti-hFasL human antibody, or antigen-binding portion thereof, that inhibits FasL-mediated apoptosis in an in vitro neutralization assay with an $IC_{50}$ of 10 nM or less (alternatively 9 nM or less, 8 nM or less, 7 nM or less, 6 nM or less, or 5 nM or less) for membrane-bound FasL, or an $IC_{50}$ of 0.2 nM or less (alternatively 0.19 nM or less, 0.18 nM or less, 0.17 nM or less, or 0.15 nM or less) for soluble FasL. Such an antigen-binding portion of the invention may exist alone or within a hFasL human antibody. In a more preferred embodiment, the isolated anti-hFasL human antibody binds a soluble FasL polypeptide with an equilibrium dissociation constant, $K_D$, of $1\times10^{-7}$ M or less, more preferably $1\times10^{-8}$ M or less, even more preferably $1\times10^{-9}$ M or less (as determined by solid phase BIAcore® at room temperature). Examples of anti-hFasL human antibodies that meet the aforementioned kinetic and neutralization criteria include 3E1 and 4G11 antibodies, as described in Examples 1, 2, and 3.

The most preferred anti-hFasL human antibody of the present invention is that referred to herein as 3E1. The 3E1 antibody has LCVR and HCVR comprising a polypeptide with a sequence as shown in SEQ ID NO: 2 and SEQ ID NO: 10, respectively (see Tables 1 and 3 herein). Exemplary polynucleotide sequences encoding the LCVR and HCVR of 3E1 are shown in SEQ ID NO: 1 and SEQ ID NO:9, respectively.

In another embodiment, a preferred anti-hFasL human antibody is that referred to herein as 4G11. The 4G11 antibody has LCVR and HCVR comprising a polypeptide with a sequence as shown in SEQ ID NO: 2 and SEQ ID NO:18, respectively (see Tables 2 and 3 herein). Exemplary polynucleotide sequences encoding the LCVR and HCVR of 4G11 are shown in SEQ ID NO: 1 and SEQ ID NO: 17, respectively.

In another embodiment, the invention provides an isolated anti-hFasL human antibody Fab and an anti-hFasL human antibody F(ab')$_2$ fragment comprising a HCVR comprising a polypeptide with the amino acid sequences of SEQ ID NO:10 or SEQ ID NO: 18, and further comprising an LCVR comprising a polypeptide with the amino acid sequence of SEQ ID NO:2 for each antibody, 3E1 and 4G11. In yet another embodiment, the invention provides isolated anti-hFasL human antibody, or antigen-binding portions thereof, comprising at least one, preferably at least 2, 3, 4 5 or 6 polypeptides with an amino acid sequence selected from the group consisting of SEQ ID NOs: 4, 6, 8, 12, 14, 16, 20, 22, and 24. Preferably, the amino acid sequence as shown SEQ ID NOs: 4, 12 or 20, when it exists in an antibody of the invention, is located at CDR1. Preferably the amino acid sequence as shown in SEQ ID NOs: 6, 14 or 22, when it exists in an antibody of the invention, is located at CDR2. And, preferably the amino acid sequence as shown in SEQ ID NOs: 8, 16, or 24, when it exists in an antibody of the invention, is located at CDR3. Preferred embodiments provide an isolated anti-hFasL human antibody, or antigenic-binding portion thereof, that inhibits soluble FasL-induced apoptosis in an in vitro neutralization assay with an $IC_{50}$ of 0.5nM or less, more preferably about 0.3 or less, more preferably about 0.15 nM or less; or membrane-bound FasL-induced proliferation or apoptosis in an in vitro neutralization assay with an $IC_{50}$ of 10 nM or less, preferably about 9, 8, 7, 6 or 5 nM or less.

In another embodiment, the present invention is also directed to cell lines that produce an anti-hFasL human antibody described herein. Isolation of cell lines producing a monoclonal antibody of the invention can be accomplished using routine screening techniques known in the art. Several cell lines that produce an anti-hFasL human antibody of the present invention have been deposited with ATCC (American Type Culture Collection). A mouse hybridoma secreting human IgG4 kappa (from a HuMab-mouse®) 3E1 is assigned reference number ATCC PTA-4017, and a mouse hybridoma secreting human IgG4 kappa (from a HuMab-mouse®) 4G11 is assigned reference number ATCC PTA-4018. Most preferred anti-hFasL human antibodies of the present invention have the same, or a substantially similar, amino acid sequence within at least 1, more preferably at least 2, 3, 4, 5 or 6 hypervariable regions (i.e., CDRs) as present in one or more of the above-mentioned ATCC deposited antibodies.

A wide variety of host expression systems can be used to express an antibody of the present invention including prokaryotic (bacterial) and eukaryotic expression systems (such as yeast, baculoviral, plant, mammalian and other animal cells, transgenic animals, and hybridoma cells), as well as phage display expression systems. An example of a suitable bacterial expression vector is pUC119 (Sfi), and a suitable eukaryotic expression vector is a modified pcDNA3.1 vector with a weakened DHFR selection system. Other antibody expression systems are also known in the art and are contemplated herein. Numerous suitable mammalian host cells are known in the art including, but not limited to, COS, CHO, NSO and 293 cells.

An antibody of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell. Preferably, the recombinant antibodies are secreted into the medium in which the host cells are cultured, from which the antibodies can be recovered. Standard recombinant DNA methodologies are used to obtain antibody heavy and light chain genes, incorporate these genes into recombinant expression vectors, and introduce the vectors into host cells. Such standard recombinant DNA technologies are described, for example, in Sambrook, Fritsch, and Maniatis (Eds.), *Molecular Cloning; A Laboratory Manual*, Second Edition, Cold Spring Harbor, N.Y., (1989); Ausubel, et al (Eds.) *Current Protocols in Molecular Biology*, Greene Publishing Associates, (1989); and in U.S. Pat. No. 4,816, 397 by Boss, et al.

An isolated DNA encoding a HCVR region can be converted to a full-length heavy chain gene by operably linking the HCVR-encoding DNA to another DNA molecule encoding heavy chain constant regions (CH1, CH2, and CH3). The sequences of human heavy chain constant region genes are known in the art. See, e.g., Kabat, et al., *Sequences of proteins of Immunological Interest*, Fifth Edition, U.S. Department of Health and Human Services, NIH Publication No. 91-3242 (1991). DNA fragments encompassing these regions can be obtained by standard PCR amplification. The heavy chain constant region can be an IgG1, IgG2, IgG3, IgG4, IgA, IgE, IgM or IgD constant region and any allotypic variant thereof as described in Kabat (supra), but most preferably is an IgG4 or an IgG1 constant region. Alternatively, the antigen binding portion can be a Fab fragment, a F(ab')$_2$ fragment, or a single chain Fv fragment (scFv). For a Fab fragment heavy chain gene, the HCVR-encoding DNA can be operably linked to another DNA molecule encoding only a heavy chain CH1 constant region.

An isolated DNA encoding a LCVR region can be converted to a full-length light chain gene (as well as a Fab light chain gene) by operably linking the LCVR-encoding DNA to another DNA molecule encoding a light chain constant region, CL. The sequences of human light chain constant region genes are known in the art. See, e.g., Kabat, supra. DNA fragments encompassing these regions can be obtained by standard PCR amplification. The light chain constant region can be a kappa or lambda constant region.

To create an scFv gene, the HCVR- and LCVR-encoding DNA fragments are operably linked to another fragment encoding a flexible linker, e.g., encoding the amino acid sequence $(Gly_4-Ser)_3$, such that the HCVR and LCVR sequences can be expressed as a contiguous single-chain protein, with the LCVR and HCVR regions joined by the flexible linker. See, e.g., Bird, et al., *Science* 242:423-6 (1988); Huston, et al., *Proc. Natl. Acad. Sci. USA* 85:5879-83 (1988); McCafferty, et al., *Nature* 348:552-4 (1990).

To express an antibody of the invention, a DNA encoding a partial or full-length light and/or heavy chain, obtained as described above, are inserted into an expression vector such that the gene is operably linked to transcriptional and translational control sequences. In this context, the term "operably linked" is means that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods. Additionally, the recombinant expression vector can encode a signal peptide that facilitates secretion of the anti-hFasL human antibody light and/or heavy chain from a host cell. The anti-hFasL human antibody light and/or heavy chain gene can be cloned into the vector such that the signal peptide is operably linked in-frame to the amino terminus of the antibody chain gene. The signal peptide can be an immunoglobulin signal peptide or a heterologous signal peptide.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma virus.

In addition to the antibody heavy and/or light chain genes and regulatory sequences, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (DHFR) gene (for use in DHFR-minus host cells with methotrexate selection/amplification), the neo gene (for G418 selection), and glutamine synthetase (GS) in a GS-negative cell line (such as NS0) for selection/amplification.

For expression of the light and/or heavy chains, the expression vector(s) encoding the heavy and/or light chains is transfected into a host cell by standard techniques e.g., electroporation, calcium phosphate precipitation, DEAE-dextran transfection and the like. Although it is theoretically possible to express the antibodies of the invention in either prokaryotic or eukaryotic host cells, preferably eukaryotic cells, and most preferably mammalian host cells, because such cells, are more likely to assemble and secrete a properly folded and immunologically active antibody. Preferred mammalian host cells for expressing the recombinant antibodies of the invention include Chinese Hamster Ovary (CHO cells) (including DHFR-CHO cells, described in Urlaub and Chasin, *Proc. Natl. Acad. Sci. USA* 77:4216-20 (1980), used with a DHFR selectable marker, e.g., as described in Kaufman and Sharp, *J. Mol. Biol.* 159:601-21 (1982)), NS0 myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the host cell and/or the culture medium using standard purification methods.

Host cells can also be used to produce portions, or fragments, of intact antibodies, e.g., Fab fragments or scFv molecules. It will be understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all the DNA encoding either or both of the light and heavy chains that is not necessary for binding to hFas Ligand. The molecules expressed from such truncated DNA molecules are also encompassed by the antibodies of the invention.

In a preferred system for recombinant expression of an antibody of the invention, a recombinant expression vector encoding both the antibody heavy chain and the antibody light chain is introduced into DHFR-CHO cells by calcium phosphate-mediated transfection. Within the recombinant expression vector, the antibody heavy and light chain genes are each operably linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of cells, e.g., CHO cells, that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Antibodies, or antigen-binding portions thereof, of the invention can be expressed in an animal (e.g., a mouse) that is transgenic for human immunoglobulin genes (see, e.g., Taylor, et al., *Nucleic Acids Res.* 20:6287-95(1992)). Plant cells can also be modified to create transgenic plants that express the antibody, or an antigen-binding portion thereof, of the invention.

In view of the foregoing, another embodiment of the invention pertains to nucleic acids, vectors, and host cell compositions that can be used for recombinant expression of the antibodies and antibody portions of the invention. Preferably, the invention provides isolated nucleic acids that comprise a region encoding one or more CDRs of 3E1 or 4G11 and even more preferably those CDRs exist in the expressed protein (e.g., antibody or antigen binding portion thereof) at the same CDR site within the antibody structure as they exist in antibody 3E1 or 4G11. Preferably, the invention provides isolated nucleic acids that comprise a region encoding the heavy chain variable region of 3E1 or 4G11 and/or the light chain variable region of 3E1 or 4G01. Accordingly, in one embodiment, the invention provides an isolated nucleic acid encoding a polypeptide comprising an antibody heavy chain variable region of 3E1 heavy chain CDR3 with a sequence as shown in SEQ ID NO: 16 and/or a heavy chain CDR2 with a sequence as shown in SEQ ID NO: 14 and/or the 3E1 heavy chain CDR1 with the sequence as shown in SEQ ID NO: 12. Most preferably, the isolated nucleic acid encodes a polypeptide comprising an antibody heavy chain variable region with a sequence as shown in SEQ ID NO:10 (the full HCVR region of 3E1).

In another embodiment, the invention provides an isolated nucleic acid encoding a polypeptide comprising a heavy chain variable region of the 4G11 heavy chain CDR3 with a sequence as shown in SEQ ID NO: 24 and/or the 4G(11 heavy chain CDR2 with a sequence as shown in SEQ ID NO: 22 and/or the 4G11 heavy chain CDR1 with sequence as shown in SEQ ID NO: 20. Even more preferably, the isolated nucleic acid encodes a polypeptide comprising an antibody heavy chain variable region comprising the sequence as shown in SEQ ID NO: 18 (the full HCVR region of 4G(11).

It is contemplated that the heavy chain and/or light chain present in an antibody of the invention may comprise various combinations of the CDRs of the invention, e.g., CDR1 and CDR2; CDR1 and CDR3; CDR2 and CDR3; or CDR1, CDR2 and CDR3. (CDR1 with a sequence as shown in SEQ ID NOs: 4, 12 or 20; CDR2 with a sequence as shown in SEQ ID NOs: 6, 14 or 22; CDR3 with a sequence as shown in SEQ ID NOs: 8, 16 or 24). Preferably the CDR sequences, when they exist in an antibody of the invention, exist at the same CDR position, in an antibody of the invention as they do in antibody 3E1 or 4G11. It is contemplated that the CDRs may exist in different chains in other antibodies of the invention than they do in antibody 3E1 or 4G11. However, most preferably, the CDR sequences when they exist in an antibody of the invention, exist at the same CDR position and in the same chain (light or heavy) as they do in antibody 3E1 or 4G11.

In still another embodiment, the invention provides an isolated nucleic acid encoding an antibody light chain variable region comprising the amino acid sequence of SEQ ID NO: 2 (i.e., the 3E1 or 4G11 LCVR). Preferably this nucleic acid comprises the nucleotide sequence of SEQ ID NO: 1, although the skilled artisan will appreciate that due to the degeneracy of the genetic code, other nucleotide sequences can encode the amino acid sequence of SEQ ID NO: 2. The nucleic acid can encode only the LCVR or can also encode an antibody light chain constant region, operably linked to the LCVR. In one embodiment, this nucleic acid is in a recombinant expression vector.

In still another embodiment, the invention provides an isolated nucleic acid encoding an antibody heavy chain variable region comprising the amino acid sequence of SEQ ID NO: 10 (i.e., the 3E1 HCVR). This nucleic acid may comprise the nucleotide sequence of SEQ ID NO: 9, although the skilled artisan will appreciate that due to the degeneracy of the genetic code, other nucleotide sequences can encode the amino acid sequence of SEQ ID NO: 10. The nucleic acid can encode only the HCVR or can also encode e.g., a heavy chain constant region, operably linked to the HCVR. For example, the nucleic acid can comprise an IgG4 or an IgG1 constant region. In one embodiment, this nucleic acid is in a recombinant expression vector.

In still another embodiment, the invention provides an isolated nucleic acid encoding an antibody heavy chain variable region comprising the amino acid sequence of SEQ ID NO: 18 (i.e., the 4G11 HCVR). This nucleic acid may comprise the nucleotide sequence of SEQ ID NO: 17, although the skilled artisan will appreciate that due to the degeneracy of the genetic code, other nucleotide sequences can encode the amino acid sequence of SEQ ID NO: 18. The nucleic acid can encode only the HCVR or can also encode a heavy chain constant region, operably linked to the HCVR. In another embodiment, this nucleic acid is in a recombinant expression vector.

The invention also provides recombinant expression vectors encoding both an antibody heavy chain and an antibody light chain. For example, in one embodiment, the invention provides a recombinant expression vector encoding:
  a) an antibody heavy chain having a variable region comprising the amino acid sequence selected from the group consisting of SEQ ID NOs: 10 and 18; and
  b) an antibody light chain having a variable region comprising the amino acid sequence of SEQ ID NO: 2.

The invention also provides host cells into which one or more of the recombinant expression vectors of the invention have been introduced. Preferably, the host cell is a mammalian host cell, more preferably the host cell is a CHO cell, an NS0 cell or a COS cell. Still further the invention provides a method of synthesizing a recombinant human antibody of the invention by culturing a host cell of the invention in a suitable culture medium until a recombinant human antibody of the invention is synthesized. The method can further comprise isolating the recombinant human antibody from the culture medium, the host cell, or both.

Once expressed, the whole antibodies, their dimers, individual light and heavy chains, or other immunoglobulin forms of the present invention can be purified according to standard procedures of the art, including ammonium sulfate precipitation, ion exchange, affinity, reverse phase, hydrophobic interaction column chromatography, gel electrophoresis and the like. Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically or prophylactically, as directed herein.

The antibodies or antibody fragments of the present invention can be incorporated into pharmaceutical compositions suitable for administration to a subject. Typically, the pharmaceutical composition comprises an antibody or antibody portion of the invention and a pharmaceutically acceptable diluent, carrier, and/or excipient. The pharmaceutical compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate.

A pharmaceutical composition comprising an anti-hFasL human antibody of the present invention can be administered to a mammal at risk for or exhibiting pathologies associated with Fas-FasL interactions using standard administration techniques by intravenous, intraperitoneal, subcutaneous, pulmonary, transdermal, intramuscular, intranasal, buccal, sublingual, or suppository administration.

The antibodies of the invention can be incorporated into a pharmaceutical composition suitable for parenteral administration. Peripheral systemic delivery by intravenous or intraperitoneal or subcutaneous injection is preferred. Suitable vehicles for such injections are straightforward and known in the art.

The pharmaceutical compositions typically must be sterile and stable under the conditions of manufacture and storage. Therefore, pharmaceutical compositions may be sterile filtered after making the formulation, or otherwise made microbiologically acceptable. A typical composition for intravenous infusion could have a volume as much as 250 mL of fluid, such as sterile Ringer's solution, and 1 to 100 mg/mL, or more in antibody concentration. Therapeutic agents of the invention can all be frozen or lyophilized for storage and reconstituted in a suitable sterile carrier prior to use. Lyophilization and reconstitution can lead to varying degrees of antibody activity loss (e.g., with conventional immunoglobulins, IgM antibodies tend to have greater activity loss than IgG antibodies). Dosages may have to be adjusted to compensate. Generally, pH between 6 and 8 is preferred.

FasL plays a critical role in the pathology associated with a variety of diseases involving immune and inflammatory factors. Therefore, a pharmaceutical composition comprising an anti-hFasL human antibody of the invention can be used to treat or prevent autoimmune and inflammatory diseases including, but not limited to, systemic inflammatory response syndrome, sepsis, multiple organ dysfunction syndrome, acute respiratory distress syndrome, severe sepsis, trauma, graft-versus-host disease, organ rejection associated with organ transplant, multiple sclerosis, idiopathic pulmonary fibrosis, osteoarthritis, inflammatory bowel disease, Crohn's disease, ulcerative colitis, acute myocardial infarction, cardiomyopathy, cardiac reperfusion injury, diabetes, cancers (including e.g., cancers which express FasL as a mechanism of evading the immune response and cancer types such as breast cancer, melanoma, ovarian cancer, colon cancer, NSCLC, lymphoma and hepatocellular carcinoma), human immunodeficiency virus, influenza virus and hepatic disorders including but not limited to fulminant viral hepatitis B or C, chronic hepatitis C virus, chronic hepatitis B virus, alcoholic hepatitis, and hepatic cirrhosis, and renal disorders including, but not limited to, acute renal disease, chronic renal disease, diabetic nephropathy.

The use of an anti-hFasL human antibody of the present invention for the treatment of at least one of the aforementioned disorders in which FasL activity is detrimental is also contemplated herein. Additionally, the use of the antibody of an anti-hFasL human antibody of the present invention for use in the manufacture of a medicament for the treatment of at least one of the aforementioned disorders in which FasL activity is detrimental is contemplated.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

A pharmaceutical composition of the invention preferably is a "therapeutically effective amount" or a "prophylactically effective amount" of an antibody of the invention. A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. A therapeutically effective amount is also one in which any toxic or detrimental effect of the antibody, or antigen-binding portion thereof, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g. a therapeutic or prophylactic response). For example, a single bolus may be administered, several divided doses may be administered over time or the dose may be proportionally reduced or increased as indicated by the exigencies of the therapeutic situation.

Given their ability to bind to hFasL, antibodies of the invention can be used to detect FasL polypeptides (e.g., in a biological sample, such as serum or plasma), using a conventional immunoassay, such as an enzyme linked immunosorbent assays (ELISA), a radioimmunoassay (RIA) or tissue immunohistochemistry. The invention provides a method for detecting FasL in a biological sample comprising contacting a biological sample with an antibody, or antibody portion, of the invention and detecting either the antibody (or antibody portion) bound to hFasL or unbound antibody (or antibody portion), to thereby detect hFasL in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, betagalactosidase, or acetylcholinesterase; examples of suitable prosthetic group complexes include streptavidin/biotin and avidinlbiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of a radioactive material include $^{125}I$, $^{131}I$, $^{35}S$, or $^{3}H$.

FasL can be assayed in biological fluids by a competition immunoassay utilizing FasL standards labeled with a detectable substance and an unlabeled anti-hFasL human antibody.

In this assay, the biological sample, the labeled FasL standards and the anti-hFasL human antibody are combined and the amount of labeled FasL standard bound to the unlabeled antibody is determined. The amount of FasL in the sample is inversely proportional to the amount of labeled FasL standard bound to the anti-hFasL human antibody.

An anti-hFasL antibody of the present invention may be used in a diagnostic assay for FasL expression. Various diagnostic assay techniques known in the art may be used, such as competitive binding assays, direct or indirect ELISA sandwich assays and immunoprecipitation assays conducted in either heterogeneous or homogeneous phases. See, e.g., Zola, *Monoclonal Antibodies: A Manual of Techniques*, CRC Press, Inc. (1987) pp. 147-158. The antibody used in the assay can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound (such as fluorescein isothiocyanate, rhodamine, or luciferin), or an enzyme (such as alkaline phosphatase, β-galactosidase or horseradish peroxidase). Any method known in the art for conjugating the antibody to the detectable moiety may be employed.

EXAMPLE 1

Functional Activity Determined Using a Jurkat Assay with Soluble hFasL

FasL/enhancer media is prepared at 4× concentration. 1× media contains 50 ng/ml recombinant human soluble FasL (Alexis® Biochemicals, Catalog #522-001) and 1 μg/ml anti-FLAG M2 mouse monoclonal antibody (enhancer; Sigma Chemical Co., Catalog #F-3165) in Jurkat cell assay media (DMEM:F-12 (3:1), 10% FBS, 20 mM HEPES, and 50 μg/mL Gentamicin). 1× media is used as the "100% apoptosis" control. Jurkat cell media without FasL or enhancer is used as the "0% apoptosis" control.

The media is incubated at room temperature for one hour. For each determination, 25 μl of either 4× enhanced Fas Ligand media or a control sample are added to each well in a 96-well plate. Next, 25 μl of either an inhibitor sample (3E1 or 4G11 anti-hFasL antibody) or a control sample is added to each well. This addition dilutes all samples and media to one-half the original concentration. Samples are incubated 45 to 60 minutes at room temperature. Next, 50 μl of Jurkat cells, at a concentration of $10^6$ cells/ml of solution, are added to each well. This addition yields 1× enhanced FasL, samples at one-fourth their initial concentration, and $5×10^4$ Jurkat cells/well. The plates are incubated for three hours at 37° C. in 5% carbon dioxide. WST-1 Cell Proliferation Reagent (Roche, Catalog #1 644 807) is added at a concentration of 10 μl/well. The plates are incubated again for approximately 18 hours at 37° C. in 5% carbon dioxide. Plates are then read on a spectrophotometric plate reader at an optimal wavelength of 450 nm. Results indicate that both anti-hFasL human antibodies, 3E1 and 4G11, are effective in neutralizing soluble FasL-mediated apoptosis in this assay

EXAMPLE 2

CHO-K1/Jurkat Assay with Membrane-Bound FasL

A CHO-K1 cell line stably expressing a non-cleavable version of hFasL, labeled Del.huFasL CHO-K1, is engineered to assay the ability of the antibodies 3E1 and 4G11 to block activity of membrane-associated FasL. This cell line expresses surface levels of FasL which, when co-cultured with Jurkat cells, induces Jurkat apoptosis.

Adherent CHO-1 cell media is prepared using DMEM:F-12 (3:1), 5% FBS, 40 μg/ml L-proline (Sigma), 50 μg/mL Gentamicin (Sigma), and 600 μg/ml G418. For each determination, approximately $10^4$ CHO-K1 cells (either Del.huFasL or parent CHO-K1) are added per well on 96-well plates. Cells are incubated overnight at 37° C. in 5% carbon dioxide. The media is removed, and 100 μl of either inhibitor sample (3E1 or 4G11 antibody; serial dilutions covering a range of concentrations) or control (media) are added to each well. The plates are incubated for one hour at 37° C. in 5% carbon dioxide. Fifty microliters of Jurkat cells ($2.5×10^5$ cells/well) are added to each well, and the plates are incubated for two hours at 37° C. in 5% carbon dioxide. Ten microliters of WST-1 Cell Proliferation Reagent are added per well. The plates are again incubated, for four hours at 37° C. in 5% carbon dioxide. The plates are then read on a spectrophotometric plate reader at an optimal wavelength of 450 nm. Results indicate that both antibodies, 3E1 and 4G11, are effective in blocking membrane bound FasL-mediated apoptosis in this assay.

EXAMPLE 3

Affinity Measurement of Monoclonal Antibodies

The affinity of various anti-hFasL antibodies for recombinant human soluble (rhs) FasL (Alexis® Biochemicals, Catalog #522-001) is measured using a BIAcore® 2000 instrument. The BIAcore® utilizes the optical properties of surface plasmon resonance to detect alteration in protein concentration of interacting molecules within a dextran biosensor matrix. Except where noted, all reagents and materials are purchased from BIAcore® AB (Upsala, Sweden). All measurements are performed at room temperature. Samples are dissolved in HBS-EP buffer (150 mM sodium chloride, 3 mM EDTA, 0.005% (w/v) surfactant P-20, and 10 mM HEPES, pH 7.4). Goat anti-human Fc antibody is immobilized on flow cells 1 and 2 of a B1 sensor chip at a level of 500 response units (RUs) using an amine coupling kit.

Binding of rhs FasL is evaluated using multiple analytical cycles. Each cycle is performed at a flow rate of 50 μl/minute and consisted of the following steps: injection of 10 μL of an anti-hFasL3E1 antibody at 1 μg/ml, injection of 240 μL of rhs FasL (starting at 100 nM and using two-fold serial dilutions for each cycle) followed by 20 minutes for dissociation, and regeneration using 50 μl of 10 mM glycine hydrochloride, pH 1.5. Association and dissociation rates for each cycle are evaluated using a "Langnuir 1:1 with mass transport" binding model in the BIAevaluation software.

EXAMPLE 4

HepG2 Apoptosis Assay with Recombinant Soluble Fas Ligand

A HepG2 (hepatocellular carcinoma; ATCC #HB-8065) cell line is used to assess neutralization of recombinant soluble FasL by antibodies 3E1 and 4G11. Cell media is prepared using DMEM:F-12 (3:1), 10% FBS, 20 mM HEPES, and 50 μg/ml gentamicin. For each determination, HepG2 cells are seeded on 96-well poly-D-lysine coated plates at a concentration of $1×10^4$ cells/well in 200 μl media. Cells are incubated overnight at 37° C. in 5% carbon dioxide. The media is removed, and replaced with 100 μl of media containing 60 μg/ml bleomycin sulfate (Sigma Chemical, Catalog #B8416). Plates are incubated overnight using a humidity chamber.

A stock solution of human FasL-FLAG is prepared in assay media (final concentration is 50 ng/ml FasL and 1 μg/ml anti-FLAG enhancer to form enhanced FasL). Anti-FasL antibodies are added to a portion of the stock solution to prepare enhanced FasL media with inhibitor. Each solution is incubated for one hour at room temperature. For 100% apoptosis control samples, 50 μl/well of the enhanced FasL solution are added to the bleomycin-containing media already in the wells. For inhibitor samples, 100 μl/well of the enhanced FasL plus antibody solution are added to the bleomycin-containing media already in the wells. The plates are then incubated overnight at 37° C. in 5% carbon dioxide.

A one to one dilution of WST-1 Cell Proliferation Reagent and media is made. Twenty microliters of diluted WST-1 are added to each well. The plates are again incubated overnight at 37° C. in 5% carbon dioxide. The plates are then read on a spectrophotometric plate reader at an optimal wavelength of 450 nm. Results indicate that as the concentration of antibody decreases, apoptosis increases.

EXAMPLE 5

Cloning and Sequencing of Heavy and Light Chain Antigen Binding Regions

The variable region for the heavy and light chain for the neutralizing human mAb 3E1 are cloned and sequenced using the following protocols.

mRNA is prepared from $2 \times 10^6$ hybridoma cells using the Micro-Fast Track protocol (Invitrogen) supplied with the kit. cDNA is prepared from 200 μl ethanol precipitate of mRNA using cDNA Cycle kit (Invitrogen) by spinning the aliquot of mRNA for thirty minutes at 14,000 rpm at 4° C. followed by washing the pellet with 70% ethanol. The air-dried pellet is resuspended in 11.5 μl of sterile water, and cDNA is prepared following the kit's instructions. The cDNA is precipitated using ethanol then resuspended in 30 μl water for use in PCR.

"The PCR reactions are set up with degenerate primers at the 5' end of the variable region for the heavy and light chain paired with the 3' primers in the constant region. For each 50 μl reaction, 1 μl cDNA is used. The reaction is set up as directed for use with Pfu I followed by twenty cycles. The PCT products are checked by running 5 μl of each reaction on a 2% agarose gel. The positive reactions are cloned using the Zero Blunt ™ TOPO ™ PCR cloning kit (Invitrogen). Minipreps from the positive clones are sequenced and analyzed for productive gene rearrangements."

EXAMPLE 6

Primary Rat Hepatocyte Assay

Apoptosis plays a role in toxic liver damage, fulminant liver failure, hepatocellular carcinoma, immune-mediated liver disease, and viral hepatitis (Kanzler and Galle, *Seminars Cancier Biol.* 10(3): 173-84 (2000)). Previous studies have demonstrated that primary human hepatocytes are susceptible to apoptosis induced by FasL. More easily attainable rat primary hepatocytes have indicated that these cells are equally susceptible to apoptosis induced by hFasL. This assay system is used to demonstrate that rat hepatocyte death and caspase activation, indicative of intracellular signaling induced by Fas-FasL interaction, is inhibited by anti-hFasL human monoclonal antibodies, 3E1 and 4G11.

Rat primary hepatocytes in matrigel in 12-well plates at $7 \times 10^5$ cells/well are purchased (In Vitro Technologies, Catalog #M00717MG). The cells are incubated for either four or twenty-four hours in the following conditions: (1) unstimulated, (2) human FasL stimulated, (3) hFasL stimulated plus FasL inhibited.(using 3E1 and 4G11 antibodies), or (4) hFasL stimulated plus caspase 3 inhibited. These cells are analyzed according to two assays: (a) lactate dehydrogenase analysis, and (b) caspase 3/8 analysis, exemplified as Example 6a and 6b, respectively. Lactate dehydrogenase release from cells indicates cell death by any method. Release of caspases 3 and/or 8 from cells indicates Fas-FasL-mediated apoptosis.

EXAMPLE 6a

Lactate Dehydrogenase Analysis

Lactate Dehydrogenase LD-L20 reagent (Sigma Chemical, Catalog #228-20) is a mixture of lactate and NAD used for the quantitative, kinetic determination of lactate dehydrogenase activity. Lactate dehydrogenase catalyzes the oxidation of lactate to pyruvate with simultaneous reduction of NAD. Formation of NADH results in an increase in absorbance at $\lambda$ 340 nm. The rate of increase in absorbance at $\lambda$340 nm is directly proportional to LD activity in the sample.

In a 96-well plate, 10 μl of sample in cell culture media are mixed with 200 μl of preheated LD-L Reagent. The plate is placed into a 37° C. plate reader for a 60 second incubation period, reading the absorbance at $\lambda$ 340 nm at three time points: 0, 30, and 60 seconds. The initial absorbance reading (time point 0 seconds) is subtracted from the final absorbance reading (time point 60 seconds) to obtain $\Delta$ absorbance/minute. The $\Delta$ absorbance/minute is converted to LD activity (U/L) according to a calculation provided by the reagent supplier. Results indicate that the presence of antibody greatly reduces the release of lactate dehydrogenase from the cells, signifying a decrease in cell death.

EXAMPLE 6b

Caspase 3/8 Analysis

The ApoAlert Caspase Fluorescent Assay Kit (Clontech, Catalog #K2026-2) is used to detect the activity of specific caspases (3, 8, or 9/6), which becomes active at different stages of the apoptotic process. 7-amino-4-trifluoromethyl coumarin (AFC), conjugated to a substrate, is proteolytically cleaved by the appropriate caspase in the sample, and free AFC fluoresces at $\lambda$505 nm.

In a 96-well black plate, 50 μL of cell lysate are mixed with 50 μl of reaction buffer and 5 μl of caspase-3 or caspase-8 substrate. The mixture is incubated at 37° C. for one hour, and read in a fluorescence plate reader at $\lambda$ 400 nm excitation$\lambda$ 505 nm emission. Emissions from apoptotic samples are compared to uninduced and inhibited controls, allowing determination of the increase in protease activity. Results indicate that caspase 3/8 activation is completely inhibited in samples containing FasL plus anti-hFasL antibody.

EXAMPLE 7

Functional Activity Using Jurkat Cells With Up-Regulated Native FasL

Stimulation of Jurkat T cells with an immobilized antibody to the T cell receptor CD3 complex induces cellular activation and up-regulation of native FasL. Activation-induced cell death then occurs, which can be directly measured by assessing cell survival or active caspase 3 activity. This system was used to determine the ability of anti-FasL antibody (3E1 was used although it is contemplated that 4G11 or other antibodies of the invention may be used) to block cell death.

Non-tissue culture-treated, 96-well flat-bottomed plates were coated with anti-human CD3 antibody (50 µl/well, 1 µg/ml in PBS) at 4° C. overnight. Plates were then washed with PBS to remove non-bound antibody. Jurkat T cells were added to the wells (50,000 cells/well) alone or together with inhibitor (Antibody 3E1) or a control $IgG_4$, at various concentrations (5 µg/ml to 5 ng/ml in a final volume of 100 µl in Jurkat assay media), and incubated for 24 hours at 37° C. in 5% carbon dioxide. WST-1 reagent (available, e.g., from Panvera) was then added (10 µl/well) and plates incubated for an additional 24 hours. Plates were read on a spectrophotometric plate reader at 450 nm. WST-1 is used to measure the number of viable cells. Results indicated that the anti-hFasL antibodies used in the assay were effective in neutralizing native FasL-mediated apoptosis in this assay.

Alternatively, 24 well plates (non-tissue culture) were coated with the anti-CD3 antibody as described above. Jurkat T cells were then added (200,000 cells/well) alone or together with the inhibitor or control antibody (final volume of 400 µl) and incubated for 24 or 48 hours at 37° C. in 5% carbon dioxide. Cells were then harvested and washed. Cells were permeabilized (Cytoperm/Cytofix, Pharmingen #554722) and stained with an anti-active caspase 3-FIFC antibody (Pharmingen #559341), and cell staining assessed on a flow cytometer. Results indicated that the anti-hFasL antibodies were effective at inhibiting caspase 3 activation (caspase 3 activity leads to cellular apoptosis).

EXAMPLE 8

Anti-FasL Antibodies Inhibit Apoptosis of HIV-Infected Human T Cells

Peripheral blood T cells are usually quiescent, until an immune response is stimulated. However, peripheral T cells of HIV-infected patients display an activated phenotype, which includes up-regulation of surface Fas and induction of FasL. It is contemplated that this surface Fas-FasL interaction is responsible for loss of many of the peripheral, non-HIV infected T cells, via apoptosis. To investigate whether anti-FasL antibodies could block this cell death, the following experiment was performed.

Peripheral blood mononuclear cells (PBMC) were purified from whole blood of HIV-infected patients using Ficoll-Hypaque. Cells were added to 24 well plates at 700,000 cells/well in media alone or together with PHA (5 µg/ml) and recombinant IL-2 (50 U/ml), which further activate the cells. The cells were incubated with or without the anti-FasL antibodies (2 µg/ml to 200 ng/ml in a final volume of 500 µl). Plates were incubated for 24 hours or 72 hours at 37° C. in 5% carbon dioxide. Cells were then harvested, washed, and incubated with anti-CD4-PE antibody. The cells were then washed again, permeabilized and stained with an anti-active caspase 3-FITC antibody and cell staining assessed on a flow cytometer. Results indicated that the anti-hFasL antibodies were effective at reducing the activation of caspase 3, and therefore apoptosis, in both the CD4 positive and CD4 negative peripheral blood lymphocytes.

TABLE 1

3E1 Heavy chain variable region DNA & amino acid sequence.

```
        Q   V   Q   L   V   Q   S       G   A   E       V   K   K       P   G   A   S
    1   CAGGTGCAGC  TGGTGCAGTC  TGGAGCTGAG  GTGAAGAAGC  CTGGGGCCTC
        GTCCACGTCG  ACCACGTCAG  ACCTCGACTC  CACTTCTTCG  GACCCCGGAG

[CDR1]
        V   K   V       S   C   K       A   S   G       Y   I   F   I       R   H   G
   51   AGTGAAGGTC  TCCTGCAAGG  CTTCTGGTTA  CATCTTTATC  AGACATGGTA
        TCACTTCCAG  AGGACGTTCC  GAAGACCAAT  GTAGAAATAG  TCTGTACCAT

I   T   W   V       R   Q   A       P   G   Q       G   L   E       W   M   G   W
  101   TCACCTGGGT  GCGACAGGCC  CCTGGACAAG  GGCTTGAGTG  GATGGGATGG
        AGTGGACCCA  CGCTGTCCGG  GGACCTGTTC  CCGAACTCAC  CTACCCTACC

[CDR2]
        I   N   A   Y       N   G   N       T   N   Y       A   Q   K       V   Q   G   R
  151   ATCAACGCTT  ACAATGGTAA  CACAAACTAT  GCACAGAAGG  TCCAGGGCAG
        TAGTTGCGAA  TGTTACCATT  GTGTTTGATA  CGTGTCTTCC  AGGTCCCGTC

V   T   M       T   T   D       K   S   T       S   T   A   Y       M   E   L
  201   AGTCACCATG  ACCACAGACA  AATCCACGAG  CACAGCCTAC  ATGGAGCTGA
        TCAGTGGTAC  TGGTGTCTGT  TTAGGTGCTC  GTGTCGGATG  TACCTCGACT

R   S   L   R       S   D   D       A   A   V       Y   Y   C   A       R   E   T
  251   GGAGCCTGAG  ATCTGACGAC  GCGGCCGTGT  ATTATTGTGC  GAGAGAGACT
        CCTCGGACTC  TAGACTGCTG  CGCCGGCACA  TAATAACACG  CTCTCTCTGA

[CDR3]
        M   V   R   G       V   P   L       D   Y   W       G   Q   G       T   L   V   T
  301   ATGGTTCGGG  GAGTTCCCCT  TGACTACTGG  GGCCAGGGAA  CCCTGGTCAC
        TACCAAGCCC  CTCAAGGGGA  ACTGATGACC  CCGGTCCCTT  GGGACCAGTG
```

TABLE 1-continued

3E1 Heavy chain variable region DNA & amino acid sequence.

```
         V   S   S     A   S   T     K   G   P     V  F    P   L   A
351  CGTCTCCTCA  GCTTCCACCA  AGGGCCCATC  AGTCTTCCCC  CTGGCG
     GCAGAGGAGT  CGAAGGTGGT  TCCCGGGTAG  TCAGAAGGGG  GACCGC
```

TABLE 2

4G11 Heavy chain variable region DNA & amino acid sequence.

```
       Q   V   Q   L    V   Q   S     G   A   E     V   K   K     P   G   A   S
  1  CAGGTGCAGC  TGGTGCAGTC  TGGAGCTGAG  GTGAAGAAGC  CTGGGGCCTC
     GTCCACGTCG  ACCACGTCAG  ACCTCGACTC  CACTTCTTCG  GACCCCGGAG

[CDR1]
       V   K   V    S   C   K     A   S   G   Y    I   F   I    S   H   G
 51  AGTGAAGGTC  TCCTGCAAGG  CTTCTGGTTA  CATCTTTATC  AGTCATGGTA
     TCACTTCCAG  AGGACGTTCC  GAAGACCAAT  GTAGAAATAG  TCAGTACCAT

I   S   W   V    R   Q   A     P   G   Q     G   L   E     W   M   G   W
101  TCAGTTGGGT  GCGACAGGCC  CCTGGACAAG  GGCTTGAGTG  GATGGGATGG
     AGTCAACCCA  CGCTGTCCGG  GGACCTGTTC  CCGAACTCAC  CTACCCTACC

[CDR2]
       I   N   A    Y   S   G   N    T   N   Y    A   Q   K    L   Q   G   R
151  ATCAACGCTT  ACAGTGGTAA  CACAAACTAT  GCACAGAAGC  TCCAGGGCAG
     TAGTTGCGAA  TGTCACCATT  GTGTTTGATA  CGTGTCTTCG  AGGTCCCGTC

V   T   M    T   T   D     R   S   T     S   T   A   Y     M   E   L
201  AGTCACCATG  ACCACAGACA  GATCCACGAG  CACAGCCTAC  ATGGAGCTGA
     TCAGTGGTAC  TGGTGTCTGT  CTAGGTGCTC  GTGTCGGATG  TACCTCGACT

R   S   L   R    S   D   D     T   A   V     Y   Y   C     A   R   E   T
251  GGAGCCTGAG  ATCTGACGAC  ACGGCCGTGT  ATTACTGTGC  GAGAGAGACT
     CCTCGGACTC  TAGACTGCTG  TGCCGGCACA  TAATGACACG  CTCTCTCTGA

[CDR3]
       M   V   R    G   V   P   C    D   Y   W     G   Q   G     L   V   T
301  ATGGTTCGGG  GAGTTCCCTG  TGACTACTGG  GGCCAGGGAA  CCCTGGTCAC
     TACCAAGCCC  CTCAAGGGAC  ACTGATGACC  CCGGTCCCTT  GGGACCAGTG

V   S   S     A   S   T     K   G   P   S    V  F    P   L   A
351  CGTCTCCTCA  GCTTCCACCA  AGGGCCCATC  CGTCTTCCCC  CTGGCG
     GCAGAGGAGT  CGAAGGTGGT  TCCCGGGTAG  GCAGAAGGGG  GACCGC
```

TABLE 3

3E1 and 4G11 Light chain variable region DNA & amino acid sequence.

```
       E   I   V   L    T   Q   S     P   G   T     L   S   L     S   P   G   E
  1  GAAATTGTGT  TGACGCAGTC  TCCAGGCACC  CTGTCTTTGT  CTCCAGGGGA
     CTTTAACACA  ACTGCGTCAG  AGGTCCGTGG  GACAGAAACA  GAGGTCCCCT

[CDR1]
       R   A   T    L   S   C     R   A   S   Q   S   V   S     S   S   Y
 51  AAGAGCCACC  CTCTCCTGCA  GGGCCAGTCA  GAGTGTTAGC  AGCAGCTACT
     TTCTCGGTGG  GAGAGGACGT  CCCGGTCAGT  CTCACAATCG  TCGTCGATGA

L   A   W   Y    Q   Q   K     P   G   Q     A   P   R     L   L   I   Y
101  TAGCCTGGTA  CCAGCAGAAA  CCTGGCCAGG  CTCCCAGGCT  CCTCATCTAT
     ATCGGACCAT  GGTCGTCTTT  GGACCGGTCC  GAGGGTCCGA  GGAGTAGATA
```

TABLE 3-continued

3E1 and 4G11 Light chain variable region DNA & amino acid sequence.

```
                            CDR2
         G   A   S     S   R   A   T       G   I   P       D   R   F       S   G   S   G
151      GGTGCATCCA   GCAGGGCCAC   TGGCATCCCA   GACAGGTTCA   GTGGCAGTGG
         CCACGTAGGT   CGTCCCGGTG   ACCGTAGGGT   CTGTCCAAGT   CACCGTCACC

S   G   T       D   F   T       L   T   I       S   R   L   E       P   E   D
201      GTCTGGGACA   GACTTCACTC   TCACCATCAG   CAGACTGGAG   CCTGAAGATT
         CAGACCCTGT   CTGAAGTGAG   AGTGGTAGTC   GTCTGACCTC   GGACTTCTAA

CDR3
         F   A   V   Y       Y   C   Q       Q   Y   G   S       S   P   W   T       F   G
251      TTGCAGTGTA   TTACTGTCAG   CAGTATGGTA   GCTCACCGTG   GACGTTCGGC
         AACGTCACAT   AATGACAGTC   GTCATACCAT   CGAGTGGCAC   CTGCAAGCCG

Q   G   T   K       V   E   I       K   R   T       V   A   A   P       S   V   F
301      CAAGGGACCA   AGGTGGAAAT   CAAACGAACT   GTGGCTGCAC   CATCTGTCTT
         GTTCCCTGGT   TCCACCTTTA   GTTTGCTTGA   CACCGACGTG   GTAGACAGAA

I   F   P
351      CATCTTCCCG
         GTAGAAGGGC
```

SEQUENCE LISTING

SEQ ID NO:1 → polynucleotide sequence encoding 3E1 or 4G11 light chain variable region

GAAATTGTGTTGACGCAGTCTCCAGGCACCCTGTCTTTGTCTCCAGGGGAA

AGAGCCACCCTCTCCTGCAGGGCCAGTCAGAGTGTTAGCAGCAGCTACTTA

GCCTGGTACCAGCAGAAACCTGGCCAGGCTCCCAGGCTCCTCATCTATGGT

GCATCCAGCAGGGCCACTGGCATCCCAGACAGGTTCAGTGGCAGTGGGTCT

GGGACAGACTTCACTCTCACCATCAGCAGACTGGAGCCTGAAGATTTTGCA

GTGTATTACTGTCAGCAGTATGGTAGCTCACCGTGGACGTTCGGCCAAGGG

ACCAAGGTGGAAATCAAACGAACTGTGGCTGCACCATCTGTCTTCATCTTC

CCG

SEQ ID NO:2 → amino acid sequence encoding 3E1 or 4G11 light chain variable region

EIVLTQSPGTLSLSPGERATLSCRASQSVSSSYLAWYQQKPGQAPRLLIYG

ASSRATGIPDRFSGSGSGTDFTLTISRLEPEDFAVYYCQQYGSSPWTFGQG

TKVEIKRTVAAPSVFIFP

SEQ ID NO:3 → polynucleotide sequence encoding 3E1 or 4G11 light chain CDR1

AGGGCCAGTCAGAGTGTTAGCAGCAGCTACTTAGCC

SEQ ID NO:4 → amino acid sequence encoding 3E1 or 4G11 light chain CDR1

RASQSVSSSYLA

SEQ ID NO:5 → polynucleotide sequence encoding 3E1 or 4G11 light chain CDR2

GGTGCATCCAGCAGGGCCACT

SEQ ID NO:6 → amino acid sequence encoding 3E1 or 4G11 light chain CDR2

GASSRAT

SEQ ID NO:7 → polynucleotide sequence encoding 3E1 or 4G11 light chain CDR3

CAGCAGTATGGTAGCTCACCGTGGACG

SEQ ID NO:8 → amino acid sequence encoding 3E1 or 4G11 light chain CDR3

QQYGSSPWT

SEQ ID NO:9 → polynucleotide sequence encoding 3E1 heavy chain variable region

CAGGTGCAGCTGGTGCAGTCTGGAGCTGAGGTGAAGAAGCCTGGGGCCTCA

GTGAAGGTCTCCTGCAAGGCTTCTGGTTACATCTTTATCAGACATGGTATC

ACCTGGGTGCGACAGGCCCCTGGACAAGGGCTTGAGTGGATGGGATGGATC

AACGCTTACAATGGTAACACAAACTATGCACAGAAGGTCCAGGGCAGAGTC

ACCATGACCACAGACAAATCCACGAGCACAGCCTACATGGAGCTGAGGAGC

CTGAGATCTGACGACGCGGCCGTGTATTATTGTGCGAGAGAGACTATGGTT

CGGGGAGTTCCCCTTGACTACTGGGGCCAGGGAACCCTGGTCACCGTCTCC

TCAGCTTCCACCAAGGGCCCATCAGTCTTCCCCCTGGCG

SEQ ID NO:10 → amino acid sequence encoding 3E1 heavy chain variable region

QVQLVQSGAEVKKPGASVKVSCKASGYIFIRHGITWVRQAPGQGLEWMGWI

NAYNGNTNYAQKVQGRVTMTTDKSTSTAYMELRSLRSDDAAVYYCARETMV

RGVPLDYWGQGTLVTVSSASTKGPSVFPLA

SEQ ID NO:11 → polynucleotide sequence encoding 3E1 heavy chain CDR1

SEQUENCE LISTING-continued

AGACATGGTATCACC

SEQ ID NO:12 → amino acid sequence encoding 3E1 heavy chain CDR1

RHGIT

SEQ ID NO:13 → polynucleotide sequence encoding 3E1 heavy chain CDR2

TGGATCAACGCTTACAATGGTAACACAAACTATGCACAGAAGGTCCAGGGC

SEQ ID NO:14 → amino acid sequence encoding 3E1 heavy chain CDR2

WINAYNGNTNYAQKVQG

SEQ ID NO:15 → polynucleotide sequence encoding 3E1 heavy chain CDR3

GAGACTATGGTTCGGGGAGTTCCCCTTGACTAC

SEQ ID NO:16 → amino acid sequence encoding 3E1 heavy chain CDR3

ETMVRGVPLDY

SEQ ID NO:17 → polynucleotide sequence encoding 4G11 heavy chain variable region CAGGTGCAGCTGGTGCAGTCTGGAGCTGAGGTGAAGAAGCCTGGGGCCTCA
GTGAAGGTCTCCTGCAAGGCTTCTGGTTACATCTTTATCAGTCATGGTATC
AGTTGGGTGCGACAGGCCCCTGGACAAGGGCTTGAGTGGATGGGATGGATC
AACGCTTACAGTGGTAACACAAACTATGCACAGAAGCTCCAGGGCAGAGTC
ACCATGACCACAGACAGATCCACGAGCACAGCCTACATGGAGCTGAGGAGC
CTGAGATCTGACGACACGGCCGTGTATTACTGTGCGAGAGAGACTATGGTT
CGGGGAGTTCCCTGTGACTACTGGGGCCAGGGAACCCTGGTCACCGTCTCC
TCAGCTTCCACCAAGGGCCCATCCGTCTTCCCCCTGGCG SEQ ID NO:18 → amino acid sequence encoding 4G11 heavy chain variable region QVQLVQSGAEVKKPGASVKVSCKASGYIFISHGISWVRQAPGQGLEWMGWI
NAYSGNTNYAQKLQGRVTMTTDRSTSTAYMELRSLRSDDTAVYYCARETMV
RGVPCDYWGQGTLVTVSSASTKGPSVFPLA SEQ ID NO:19 → polynucleotide sequence encoding 4G11 heavy chain CDR1

AGTCATGGTATCAGT

SEQ ID NO:20 → amino acid sequence encoding 4G11 heavy chain CDR1

SHGIS

SEQ ID NO:21 → polynucleotide sequence encoding 4G11 heavy chain CDR2

TGGATCAACGCTTACAGTGGTAACACAAACTATGCACAGAAGCTCCAGGGC

SEQ ID NO:22 → amino acid sequence encoding 4G11 heavy chain CDR2

WINAYSGNTNYAQKLQG

SEQ ID NO:23 → polynucleotide sequence encoding 4G11 heavy chain CDR3

GAGACTATGGTTCGGGGAGTTCCCTGTGACTAC

SEQ ID NO:24 → amino acid sequence encoding 4G11 heavy chain CDR3

ETMVRGVPCDY

---

I claim:

1. An isolated anti-hFasL human antibody, or antigen-binding portion thereof, comprising a light chain variable region (LCVR) and a heavy chain variable region (HCVR), wherein the LCVR comprises the amino acid sequence shown in SEQ ID NO:2 and the HCVR comprises an amino acid sequence selected from the group consisting of SEQ ID NO: 10 and SEQ ID NO: 18.

2. The isolated anti-hFasL human antibody, or antigen-binding portion thereof, of claim 1, wherein the LCVR comprises the amino acid sequence shown in SEQ ID NO:2 and wherein the HCVR comprises the amino acid sequence shown in SEQ ID NO:10.

3. The isolated anti-hFasL human antibody, or antigen-binding portion thereof, of claim 1, wherein the LCVR comprises the amino acid sequence shown in SEQ ID NO:2 and wherein the HCVR comprises the amino acid sequence shown in SEQ ID NO: 18.

4. The isolated antibody of claim 1, which has an IgG 1 heavy chain constant region.

5. The isolated antibody of claim 1, which has an IgG4 heavy chain constant region.

6. The isolated antigen-binding portion of claim 1, which is a Fab fragment.

7. The isolated antigen-binding portion of claim 1, which is a F(ab') 2 fragment.

8. The isolated antigen-binding portion of claim 1, which is a single chain Fv fragment.

9. A method for inhibiting hFasL activity comprising contacting hFasL with the antibody or antigen-binding portion thereof of claim 1.

10. A pharmaceutical composition comprising the antibody, or antigen-binding portion thereof, of claim 1 and a pharmaceutically acceptable carrier.

11. A hybridoma selected from the group consisting of the hybridoma deposited as ATCC PTA-4017 and the hybridoma deposited as ATCC PTA-4018.

* * * * *